United States Patent
Viola et al.

(10) Patent No.: US 9,918,617 B2
(45) Date of Patent: Mar. 20, 2018

(54) MOUNTABLE CAMERA FOR LAPAROSCOPIC SURGERY

(75) Inventors: Frank Viola, Sandy Hook, CT (US); Kenneth Horton, South Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 800 days.

(21) Appl. No.: 13/210,573

(22) Filed: Aug. 16, 2011

(65) Prior Publication Data

US 2012/0108900 A1   May 3, 2012

Related U.S. Application Data

(60) Provisional application No. 61/409,275, filed on Nov. 2, 2010.

(51) Int. Cl.
| | |
|---|---|
| *A61B 1/00* | (2006.01) |
| *A61B 1/01* | (2006.01) |
| *A61B 1/05* | (2006.01) |
| *A61B 1/313* | (2006.01) |
| *A61B 90/00* | (2016.01) |
| A61B 1/018 | (2006.01) |
| A61B 1/06 | (2006.01) |
| A61B 17/00 | (2006.01) |
| A61B 90/30 | (2016.01) |

(52) U.S. Cl.
CPC .......... *A61B 1/00121* (2013.01); *A61B 1/053* (2013.01); *A61B 1/3132* (2013.01); *A61B 90/361* (2016.02); *A61B 1/01* (2013.01); *A61B 1/018* (2013.01); *A61B 1/0676* (2013.01); *A61B 1/0684* (2013.01); *A61B 17/00234* (2013.01); *A61B 2017/00477* (2013.01); *A61B 2017/00876* (2013.01); *A61B 2090/309* (2016.02)

(58) Field of Classification Search
CPC ........................................................ A61B 1/01
USPC ................ 600/114, 121–125, 141–145, 160, 600/165–166, 186, 175, 151, 112, 109, 600/106
See application file for complete search history.

(56) References Cited

U.S. PATENT DOCUMENTS

| | | |
|---|---|---|
| 5,833,611 A | 11/1998 | Tepper et al. |
| 6,004,320 A | 12/1999 | Casscells et al. |
| 6,120,496 A | 9/2000 | Whayne et al. |
| 7,029,435 B2 | 4/2006 | Nakao |
| 7,691,103 B2 * | 4/2010 | Fernandez et al. ............. 606/41 |
| 8,317,814 B2 * | 11/2012 | Karasawa et al. ............. 606/185 |
| 2002/0045884 A1 | 4/2002 | Turovskiy et al. |

(Continued)

FOREIGN PATENT DOCUMENTS

| | | | |
|---|---|---|---|
| JP | 2002204773 A | | 7/2002 |
| JP | 2003135388 A | | 5/2003 |
| JP | 20033135388 | * | 5/2003 |

(Continued)

OTHER PUBLICATIONS

European Search Report for corresponding EP11187365 dated Feb. 28, 2012 (3 pgs).

*Primary Examiner* — John P Leubecker (57) ABSTRACT

A laparoscopic surgical system comprising a camera and a base supporting the camera, and a camera insertion tool for inserting the camera into the body cavity. The camera is mountable to a surgical instrument inside the body cavity and releasable from the insertion tool after mounting to the surgical instrument.

6 Claims, 6 Drawing Sheets

(56) References Cited

U.S. PATENT DOCUMENTS

2005/0165272 A1*  7/2005  Okada et al. ................ 600/114
2006/0235457 A1*  10/2006  Belson ......................... 606/191

FOREIGN PATENT DOCUMENTS

| WO | WO2005/053517 A1 | 6/2005 |
| WO | WO2007/061386 A1 | 5/2007 |
| WO | WO2010/034107 A1 | 4/2010 |

* cited by examiner

MOUNTABLE CAMERA FOR LAPAROSCOPIC SURGERY

CROSS-REFERENCE TO RELATED APPLICATIONS

The present application claims priority to, and the benefit of, U.S. Provisional Patent Application Ser. No. 61/409,275, filed on Nov. 2, 2010, the contents of which are hereby incorporated by reference.

BACKGROUND

Technical Field

The present disclosure relates generally to a laparoscopic surgical system and more particularly to an instrument mountable camera for laparoscopic surgery.

Background of Related Art

In laparoscopic surgery, surgery is performed through access ports extending into the abdominal cavity. The advantages of laparoscopic and other minimally invasive surgical procedures are well established and include reduced infection, reduced costs and reduced patient recovery time. In many of these procedures, several access ports are required, each dimensioned to receive a surgical instrument, providing a guide for accessing the surgical site. One of the access ports is configured to receive the endoscopic camera for viewing the abdominal cavity and enabling display of the cavity and the manipulation of the instrumentation and tissue within the body cavity on a video monitor.

It would be advantageous to reduce the number of access ports in the abdominal cavity while maintaining the same instrumentation and maneuverability of the instruments within the body cavity. It would also be advantageous to alternatively provide the same number of access ports but enable use of an additional instrument within the body cavity.

SUMMARY

The present disclosure provides in one aspect a laparoscopic surgical system comprising a camera, a base supporting the camera and a camera insertion tool for inserting the camera into the body cavity through an access port. The camera is mountable to a surgical instrument inside the body cavity and releasable from the insertion tool after mounting to the surgical instrument.

In a preferred embodiment, the base includes at least one magnet for magnetic attachment of the camera to the surgical instrument. The system can include a sleeve mountable to a least a portion of the surgical instrument wherein the camera is mountable to the sleeve. Preferably, the surgical instrument can rotate about a longitudinal axis within the sleeve while the camera remains stationary on the sleeve. The base can include an opening at a proximal end to receive a distal portion of the insertion tool.

The present disclosure provides in another aspect a camera mountable to a portion of a surgical instrument extending into a body cavity through a second opening, the camera having a mounting base and at least one magnet supported by the base. The camera is insertable through a first opening in the body cavity and magnetically connectable to a portion of the surgical instrument inside the body cavity which extends through the second opening in the body cavity.

In another aspect, the present disclosure provides a method for performing laparoscopic surgery comprising providing a camera and a camera insertion tool, inserting the camera through a first access port into a body cavity, attaching the camera to a portion of a first laparoscopic instrument positioned within the body cavity, and removing the insertion tool from the camera and withdrawing the insertion tool through the first access port The method can further include the step of inserting a second laparoscopic instrument through the first access port after the step of removing the insertion tool. The first laparoscopic instrument can be inserted into the body cavity through a second access port. In a preferred embodiment, the step of attaching the camera comprises attaching the camera via at least one magnet. In one embodiment, a portion of the laparoscopic instrument includes an outer sleeve, and the step of attaching the camera to the instrument includes the step of attaching the camera to the outer sleeve.

BRIEF DESCRIPTION OF THE DRAWINGS

Various embodiments of the presently disclosed device are described herein with reference to the drawings, wherein.

DETAILED DESCRIPTION OF EMBODIMENTS

The presently disclosed laparoscopic surgical system and camera will now be described in detail with reference to the drawings in which like reference numerals designate identical or corresponding elements in each of the several views. Throughout this description, the term "proximal" will refer to the portion of the instrument closer to the operator and the term "distal" will refer to the portion of the instrument further from the operator. The presently disclosed system is particularly suited for laparoscopic surgery but the system can be utilized for other minimally invasive surgical procedures.

The surgical system of the present disclosure advantageously eliminates the need for a designated access port for a camera for visualization of laparoscopic procedures. By freeing such access port, it can be used for insertion of other surgical instruments, thus requiring one less access port which translates advantageously to one less opening in the abdominal cavity, reducing the attendant risks of such opening and reducing the patient recovery time. As described in detail below, this is achieved by providing a camera which is inserted into the body cavity and mounted to a laparoscopic instrument inside the body cavity.

The mounting of the camera directly to the laparoscopic instrument also has the advantage of improving visibility as the camera lens is aligned along a path of the end effectors of the instrument. The mounting of the camera to the instrument shaft also has the advantage that multiple cameras can be inserted into the body cavity, each mounted to a select laparoscopic instrument, without increasing the number of access ports.

The camera is mounted by a camera insertion tool described below which can then be withdrawn from the access port, leaving the port available for insertion of other instrumentation, e.g. a retractor, clip applier, etc. In the drawings and following description, mounting of the camera to a laparoscopic clip applier is shown by way of example, it being understood that the camera can be mounted to other laparoscopic/endoscopic instruments within the body cavity in a similar fashion.

Figure 1:
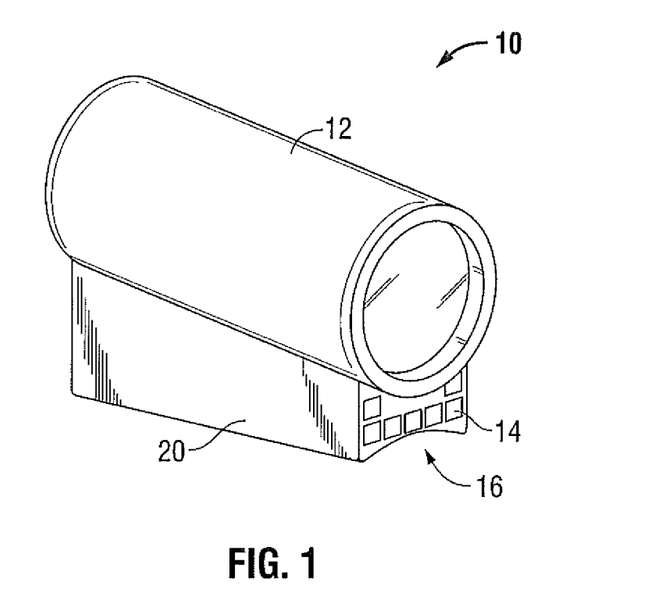
FIG. 1 is a perspective view of the mountable camera of the present disclosure.
Figure 2:
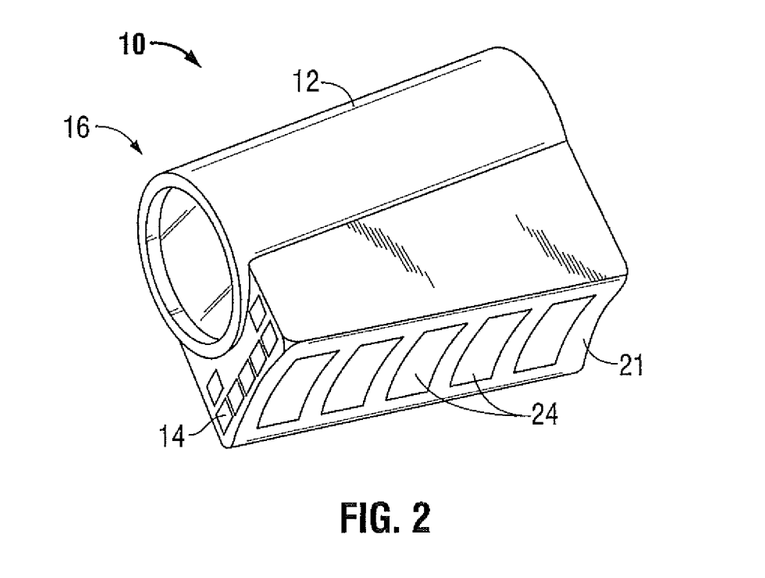
FIG. 2 is a bottom perspective view of the mountable camera of FIG. 1.

Turning first to FIGS. 1 and 2, the camera of the present disclosure is designated generally by reference numeral 10. The camera has a cylindrical body 12 with LEDs 14 at the distal end 16. The camera has a mounting base 20, preferably formed integral therewith. Mounting base 20 in one embodiment has a concave mounting surface 21 dimensioned to conform to an outer surface of a laparoscopic instrument shaft or the laparoscopic instrument sleeve described below. In alternate embodiments, the mounting surface can be flat or other configurations. Surface 21 of mounting base 20 includes a plurality of magnets 24. A different number of magnets and a different arrangement of the magnets from FIG. 1 are also contemplated. An example of another arrangement is a V-block arrangement where a V-groove would accommodate one or more magnets.

The magnets are shown positioned in the base 20. However, in alternate embodiments, the magnet(s) can be positioned inside the camera. This can avoid the need of the mounting base if desirable. Mechanical attachment methods for attaching the camera or the instrument are also contemplated.

The camera preferably has an outer diameter of about 10 mm or less.

Figure 3:
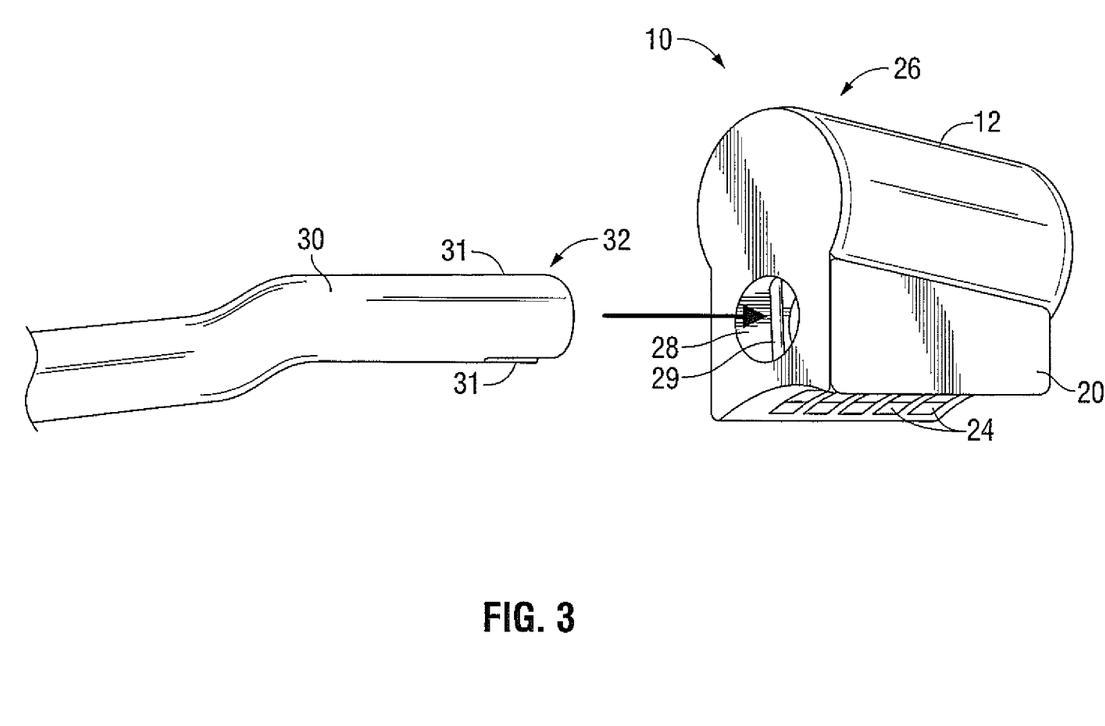
FIG. 3 is a perspective of the camera of FIG. 1 and a camera insertion tool.
Figure 5:
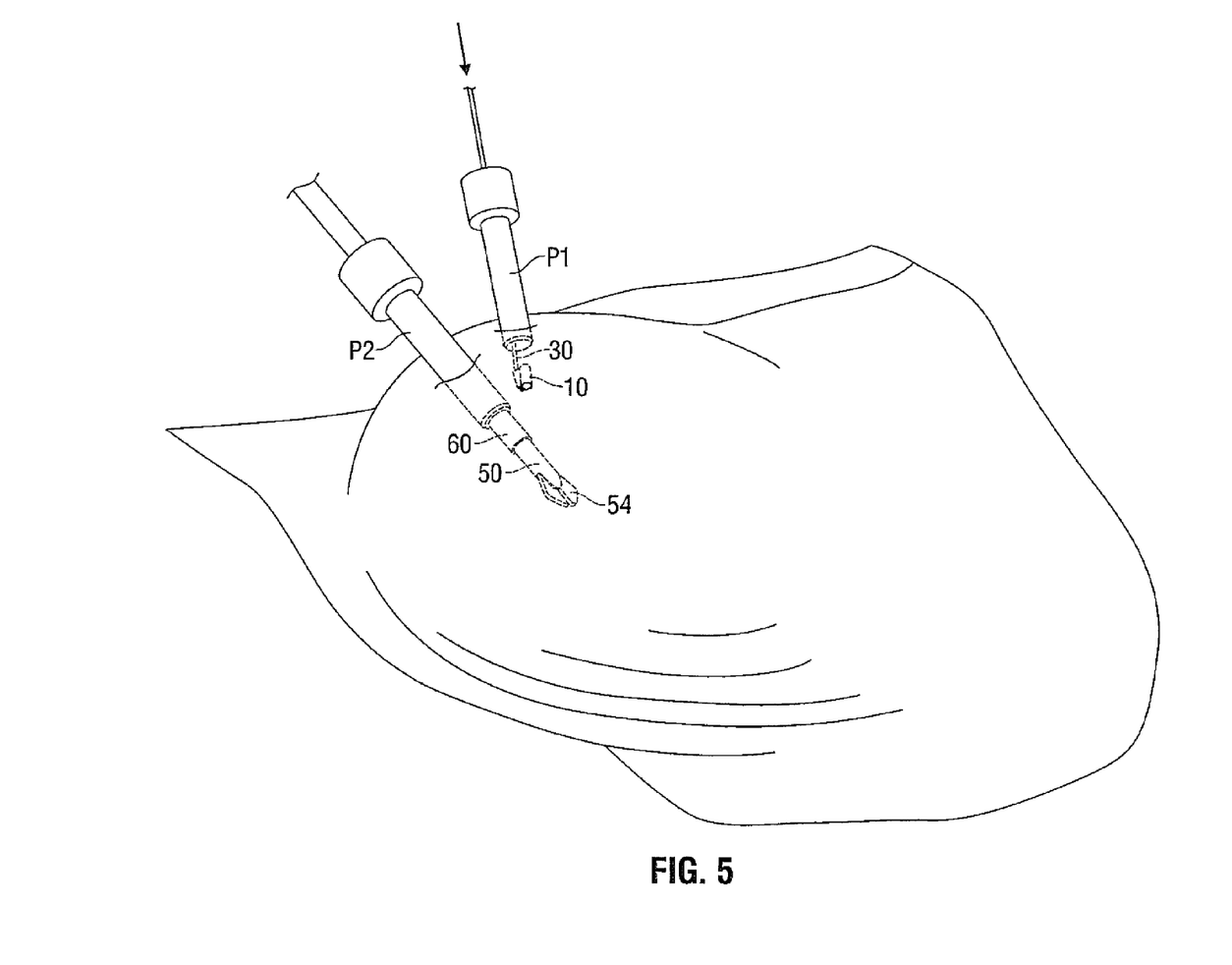
FIG. 5 illustrates the camera and insertion tool of FIG. 1 being inserted into the abdominal cavity through a laparoscopic port.

As shown in FIG. 3, the proximal end 26 of the base 20 has an opening 28 dimensioned and configured to receive camera insertion tool 30. The opening can include one or more posts 29 to enhance frictional engagement with the insertion tool 30. The distal end 32 of insertion tool 30 has opposing slots 31. The distal end 32 is inserted into opening 28 to hold the camera by a frictional fit as the posts 29 compress the slotted portion of the insertion tool 30. It is also contemplated that the insertion tool 30 can be removably connected to base 20 by other ways such as a screw thread, bayonet mount, or a hook/slot arrangement. These connections enable the camera to be securely held by the insertion tool 30 during insertion through the access port and manipulation within the body cavity for magnetic attachment to a laparoscopic instrument positioned within the body cavity, while allowing subsequent release after instrument mounting. Insertion of the camera 10 through an access port P1 is shown in FIG. 5.

The camera can alternatively be retained by other insertion tools, such as a grasper with movable or spring loaded jaws for example.

Figure 7:
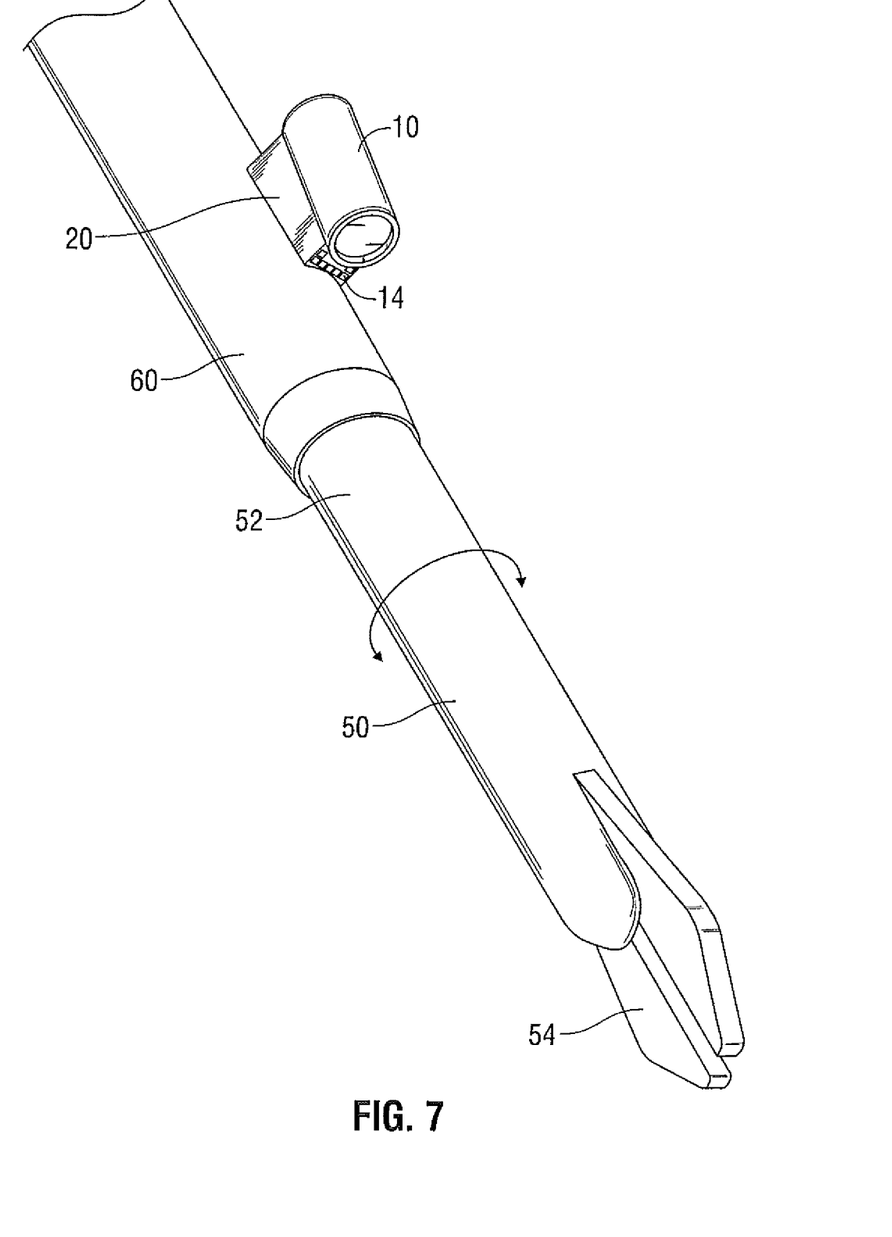
FIG. 7 illustrates the camera mounted on a sleeve of the clip applier.

Referring to FIG. 7, a distal portion of a clip applier 50 is shown. A sleeve 60 is composed of suitable material, such as stainless steel or other magnetic material that reacts to the magnetic field of magnets 24 so that the mounting base 20 is magnetically connected to the sleeve 60. This sleeve 60 is positioned around the endoscopic portion (elongated shaft) 52 of clip applier 50. In this way, the clip applier can be rotated (see arrow in FIG. 7) independent of the sleeve 60 and independent of the camera 10 so the positioning of the clip applier jaws 54 can be changed without affecting visualization as the camera 10 and lens remain stationary.

It is also contemplated that the magnet(s) can be placed inside the sleeve (which can be composed of a magnetic material) for magnetic attraction to the camera through the sleeve.

The camera 12 is preferably movable axially along the instrument to a select position along the longitudinal axis of the instrument or sleeve. For example, the camera can be moved closer to the distal tip of the instrument to zoom in on the tissue or moved away from the instrument tip to zoom out and increase the peripheral vision.

Figure 4:
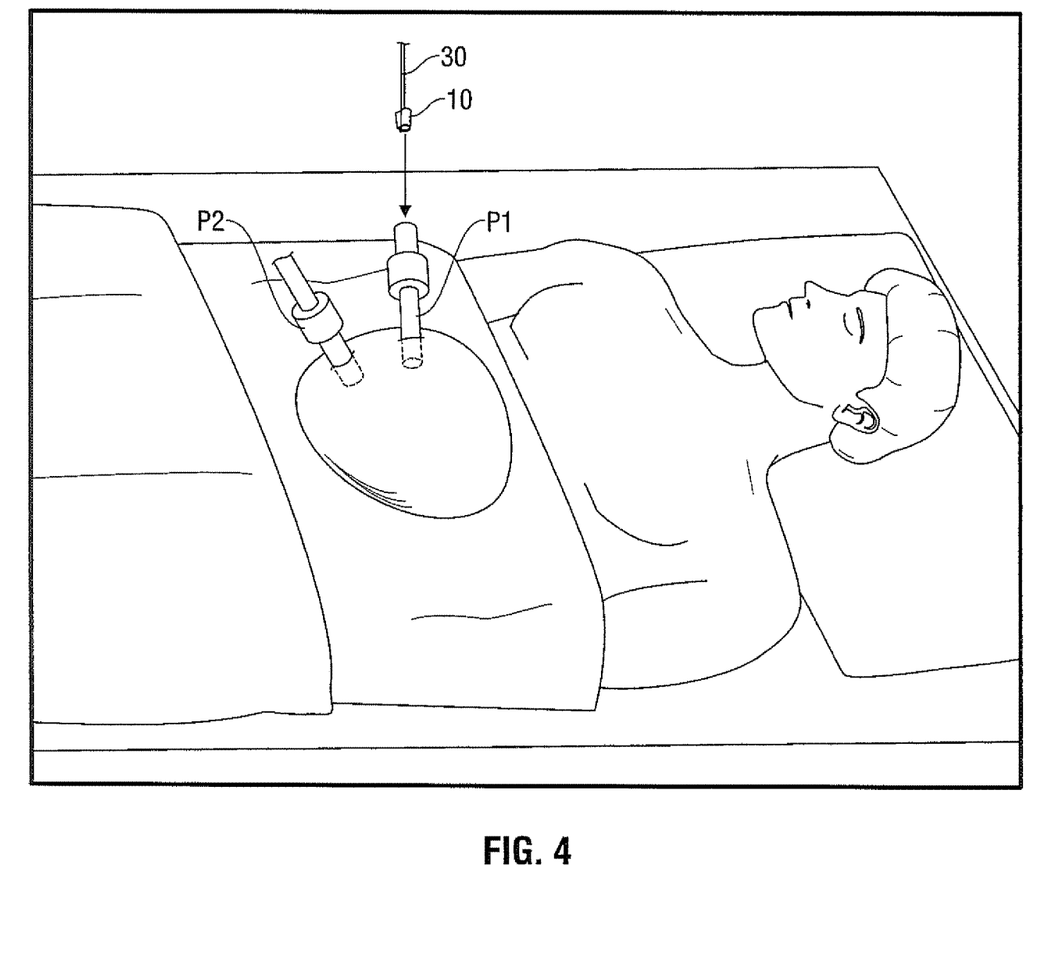
FIG. 4 illustrates the camera and insertion tool of FIG. 3 prior to insertion through a laparoscopic port.
Figure 6:
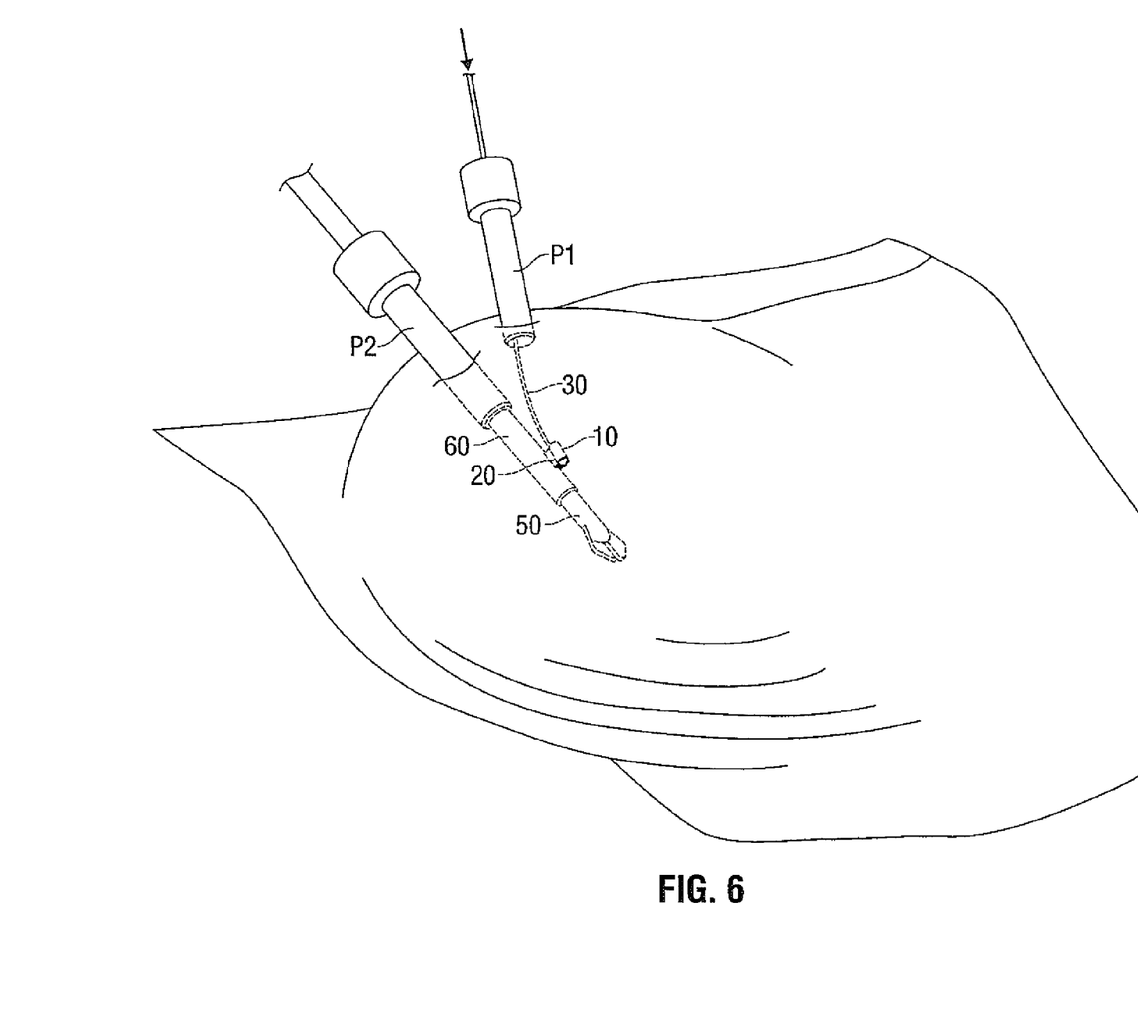
FIG. 6 illustrates the camera being mounted to a clip applier within the abdominal cavity.

The use of the system in an abdominal cavity for laparoscopic surgery will now be described, with reference to FIGS. 4-6. Note FIG. 4 illustrates two access port P1 and P2, one for camera insertion and one for instrument insertion. It is also envisioned that additional ports can be provided through other abdominal incisions. In any event, the mountable camera 10 of the present disclosure frees one of the ports after mounting the camera to the laparoscopic instrument.

Port P2 is used for insertion of a laparoscopic or endoscopic instrument, which by way of example is a clip applier 50 (FIG. 5). The insertion tool 30 with camera 10 attached is inserted through port P1 as shown in FIG. 5. The clip applier 50 is inserted into the abdominal cavity through port P2. The camera 10 is positioned on sleeve 60 and attached thereto by the magnetic attraction of magnets 24. Once placed on the sleeve 60, the clinician can pull back on the insertion tool 30 to release it from the camera 10. If a hook engagement or a threaded engagement is utilized, the insertion tool 30 can be released by reverse rotation or movement. The insertion tool 30 is then removed from the cavity through port P1, leaving the camera 10 mounted on concentric sleeve 60. The port P1 is now available for insertion of other instrumentation for performing the procedure. The camera 10 provides visualization of the tissue adjacent the clip applier jaws 52 which can then be viewed by the clinician on a video monitor. If another port is utilized (not shown) a camera 10 can be mountable on this instrument as well if desired via insertion through port P1 in the same manner as attached to the clip applier 50.

To retrieve the camera 10 at the end of the surgical procedure, the insertion tool 30 is inserted through port P1 and placed within opening 28 of mounting base 20 of camera 10 for connection thereto. The camera 10 is then released from the sleeve 60 by insertion tool 30, overcoming the magnetic force of magnets 24, and removed through port P1.

Although shown within the abdominal cavity, it can be used in other regions of the body.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A method for performing laparoscopic surgery comprising:

providing a camera and a camera insertion tool having the camera mounted thereon;

inserting the camera through a first access port into a body cavity;

attaching the camera to a portion of a first laparoscopic instrument positioned within the body cavity;

removing the insertion tool from the camera and withdrawing the insertion tool through the first access port; and performing a surgical procedure with the first laparoscopic instrument while viewing a surgical area via the camera mounted on the first laparoscopic instrument.

2. The method of claim 1, further comprising inserting a second laparoscopic instrument through the first access port after removing the insertion tool.

3. The method of claim 1, further comprising inserting the first laparoscopic instrument into the body cavity through a second access port.

4. The method of claim 1, wherein attaching the camera comprises attaching the camera via at least one magnet.

5. The method of claim 1, wherein attaching the camera to the first laparoscopic instrument includes attaching the camera to an outer sleeve of the first laparoscopic instrument.

6. The method of claim 1, further comprising moving the camera axially along the first laparoscopic instrument to a select position.

* * * * *